US010993814B2

(12) United States Patent
Wolters

(10) Patent No.: US 10,993,814 B2
(45) Date of Patent: May 4, 2021

(54) HEIGHT ADJUSTABLE SPINE IMPLANT

(71) Applicant: Life Spine, Inc., Huntley, IL (US)

(72) Inventor: Madeline C. Wolters, St. Charles, IL (US)

(73) Assignee: LIFE SPINE, INC., Huntley, IL (US)

( * ) Notice: Subject to any disclaimer, the term of this patent is extended or adjusted under 35 U.S.C. 154(b) by 0 days.

(21) Appl. No.: 16/287,003

(22) Filed: Feb. 27, 2019

(65) Prior Publication Data

US 2019/0262139 A1    Aug. 29, 2019

Related U.S. Application Data

(60) Provisional application No. 62/635,887, filed on Feb. 27, 2018.

(51) Int. Cl.
*A61F 2/44* (2006.01)
*A61F 2/30* (2006.01)

(52) U.S. Cl.
CPC .............. *A61F 2/447* (2013.01); *A61F 2/442* (2013.01); *A61F 2/4455* (2013.01);
(Continued)

(58) Field of Classification Search
CPC ............ A61F 2/447; A61F 2002/30507; A61F 2002/30556; A61F 2/442; A61F 2/4455; A61F 2002/30112; A61F 2002/30158; A61F 2002/30261; A61F 2002/30266; A61F 2002/30329; A61F 2002/30331; A61F 2002/30378; A61F 2002/30387; A61F 2002/30525; A61F 2002/30537; A61F 2002/30538; A61F 2002/30579;
(Continued)

(56) References Cited

U.S. PATENT DOCUMENTS

| 5,609,635 A * | 3/1997 | Michelson | A61F 2/442 |
| | | | 623/17.16 |
| 2015/0374507 A1* | 12/2015 | Wolters | A61F 2/446 |
| | | | 623/17.15 |

(Continued)

FOREIGN PATENT DOCUMENTS

| EP | 3050540 A1 | 8/2016 |
| WO | 2013/145176 A1 | 10/2013 |

*Primary Examiner* — Pedro Philogene
(74) *Attorney, Agent, or Firm* — Foley & Lardner LLP

(57) ABSTRACT

A variable height intervertebral spine implant is adjustable in situ having first and second trapezoidal components oriented such that the short surfaces/sides of their parallel surfaces/sides are adjacent, forming a first wedge-shaped pocket between opposing first skew surfaces/sides of the first and second components on a first end, and a second wedge-shaped pocket between opposing second skew surfaces/sides of the first and second components on a second end. First and second lateral flanges of both the first and second components cooperate to connect the first and second components together, and to allow height adjustment between the first and second components. A first wedge situated in the first pocket and a second wedge situated in the second pocket are connected via a drive mechanism that effects concerted movement thereof whereby contraction increases implant height while expansion decreases implant height. The wedges ride against the skew sides of the components.

4 Claims, 4 Drawing Sheets

(52) U.S. Cl.
CPC ........... *A61F 2002/3093* (2013.01); *A61F 2002/30112* (2013.01); *A61F 2002/30158* (2013.01); *A61F 2002/30261* (2013.01); *A61F 2002/30266* (2013.01); *A61F 2002/30326* (2013.01); *A61F 2002/30329* (2013.01); *A61F 2002/30331* (2013.01); *A61F 2002/30378* (2013.01); *A61F 2002/30387* (2013.01); *A61F 2002/30405* (2013.01); *A61F 2002/30411* (2013.01); *A61F 2002/30507* (2013.01); *A61F 2002/30525* (2013.01); *A61F 2002/30537* (2013.01); *A61F 2002/30538* (2013.01); *A61F 2002/30556* (2013.01); *A61F 2002/30579* (2013.01); *A61F 2002/30593* (2013.01); *A61F 2002/30622* (2013.01); *A61F 2002/30784* (2013.01)

(58) Field of Classification Search
CPC .. A61F 2002/30593; A61F 2002/30622; A61F 2002/30784; A61F 2002/3093
USPC ...................................................... 623/17.11
See application file for complete search history.

(56) References Cited

U.S. PATENT DOCUMENTS

| | | | |
|---|---|---|---|
| 2017/0224504 A1 | 8/2017 | Butler et al. | |
| 2017/0224505 A1* | 8/2017 | Butler | A61F 2/44 |
| 2017/0367842 A1 | 12/2017 | Predick et al. | |
| 2018/0185164 A1* | 7/2018 | Sharabani | A61F 2/447 |
| 2018/0296361 A1* | 10/2018 | Butler | A61F 2/4425 |
| 2019/0262139 A1* | 8/2019 | Wolters | A61F 2/442 |
| 2019/0343644 A1* | 11/2019 | Ryan | A61F 2/30771 |

* cited by examiner

HEIGHT ADJUSTABLE SPINE IMPLANT

CROSS-REFERENCE TO RELATED APPLICATIONS

This U.S. non-provisional patent application claims the benefit of and/or priority under 35 U.S.C. § 119(e) to U.S. provisional patent application Ser. No. 62/635,887 filed Feb. 27, 2018 titled "Height Adjustable Spine Implant," the entire contents of which is specifically incorporated herein by reference.

FIELD OF THE INVENTION

The present invention relates to implants for the spine and, more particularly, to spine implants that are adjustable in height.

BACKGROUND OF THE INVENTION

Many people contend with spine issues as a result of age, disease, and trauma, as well as congenital and acquired complications and conditions. While some of these issues can be alleviated without surgery, other issues necessitate surgery. Issues with the spine such as decompression and stabilization can be addressed with intervertebral spine implants. Intervertebral or interbody spine implants are placed within the disc space between adjacent vertebrae once disc tissue has been removed. The Intervertebral spine implant may be secured to one or both of the upper and lower vertebrae. Additionally, bone graft may or may not be used with intervertebral spine implants in order to facilitate vertebral fusion—which stops all movement between vertebrae.

The purpose of intervertebral spine implants is to maintain disc height between vertebrae to help prevent nerve compression, restore and preserve the natural alignment of the spine, and promote spinal fusion. As mentioned above, in some cases intervertebral spine implants may be a holder or carrier for fusion material. In other cases intervertebral spine implants may stand alone to provide structural stability. The spine implant may also substitute for a vertebra that has been removed partially or in full.

Because of variations in vertebral anatomy, it is desirable for intervertebral spine implants to be adjustable in height rather than static. It is also desirable for the intervertebral spine implants to be adjustable in height in situ after implantation rather than before implantation. Because there are moving parts in an intervertebral spine implant that is height adjustable, there is a need to address stability of the implant after implantation as well as other issues.

It is therefore an object of the present invention to provide an intervertebral spine implant that is adjustable in height in situ. It is also an object of the present invention to provide an in situ height adjustable intervertebral spine implant that remains stable after implantation.

The aforementioned and other objects and desires are satisfied by the present height adjustable intervertebral spine implant.

SUMMARY OF THE INVENTION

An intervertebral (interbody) spine implant is height adjustable in situ. Height adjustment creates a variable height intervertebral spine implant.

The variable height intervertebral spine implant is characterized by first and second trapezoidal components oriented to one another such that the short sides of their parallel sides are adjacent, forming a first wedge-shaped pocket on a first end between opposing first skew sides of the first and second components, and a second wedge-shaped pocket on a second end between opposing second skew sides of the first and second components. Each of the long sides of the parallel sides of the first and second trapezoidal components are configured to abut adjacent vertebral surfaces.

The first component has first and second opposing lateral flanges and the second component has first and second opposing lateral flanges, the first and second opposing lateral flanges of the first component cooperate with the first and second lateral flanges of the second component to connect the first and second components together and to allow translation between the first and second components in order to effect adjustment in height of the implant.

A first wedge situated in the first pocket and a second wedge situated in the second pocket are connected to each other via a controllable driver that effects concerted movement of the first and second wedges both towards (contraction) and away (expansion) from one another. The first wedge rides against the opposite sloped skewed sides of the first pocket defined between the first ends of the first and second components, while the second wedge rides against the opposite sloped skewed sides of the second pocket defined between the second ends of the first and second components. Contraction of the first and second wedges toward each other increases implant height by pushing against the opposite sloped skew sides of first and second pockets, while expansion of the first and second wedges away from each other decreases implant height by alleviating force against the opposite sloped skew sides of the first and second pockets.

The controllable drive or adjustment means may be characterized by a screw/screw drive that is operably coupled to and between the first and second wedges. Rotation of the screw drive in a first rotational direction pulls (contracts) the first and second wedges towards each other (inward) thereby pushing against first and second sloped skewed sides or surfaces of the first pocket to adjustably spread the first and second components relative to one another, thus increasing implant height. Rotation of the screw drive in a second rotational direction pushes (spreads) the first and second wedges away from each other (outward)—allowing the first and second components to contract relative to one another, thus reducing implant height.

In one form, the screw drive is characterized by a threaded shaft that is threadedly connected to each wedge. A configured socket at one end allows use of a like-configured tool to rotate the screw drive. In another form, the screw drive is threadedly connected to a set of spheres (one with a left handed thread form, and the other with a right handed thread form) that are captured within spherical pockets of each of the first and second wedges. As the shaft is rotated the spheres axially move along the screw drive spreading the wedges along the drive shaft which in turn forces the wedges (translating members) to be driven outward.

In one form, each of the first and second components has a central opening for bone graft. Additionally, each of the first and second components may include portions made of a matrix, mesh or porous material on the vertebral contact/abutments surfaces of the first and second components for fusion material and/or promoting/facilitating bony ingrowth.

BRIEF DESCRIPTION OF THE DRAWINGS

The features of the invention will be better understood by reference to the accompanying drawings which illustrate two forms of the invention, wherein.

DETAILED DESCRIPTION OF THE INVENTION

Figure 1:
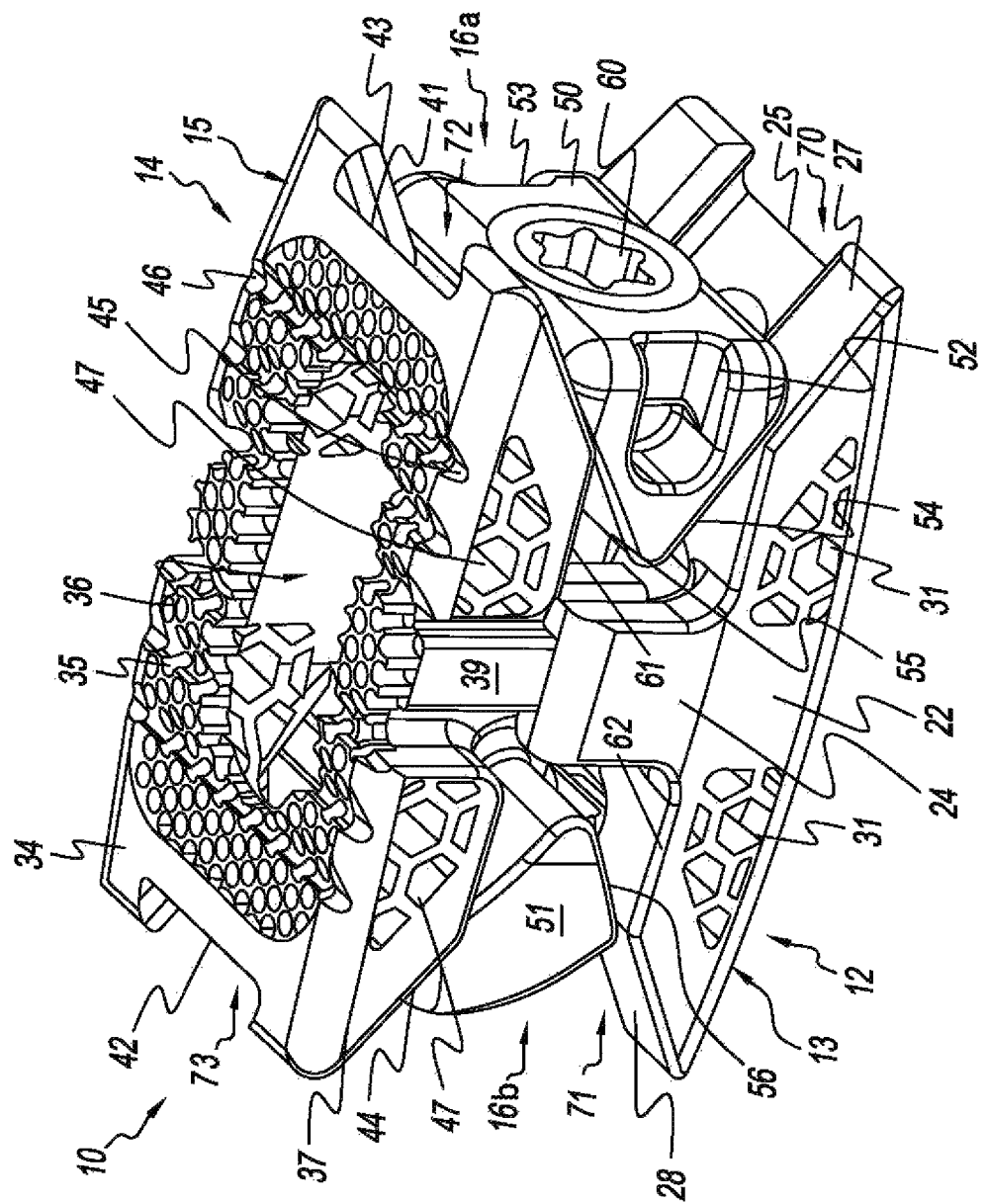
FIG. 1 is an isometric view of one form of an intervertebral spine implant fashioned in accordance with the present principles.
Figure 2:
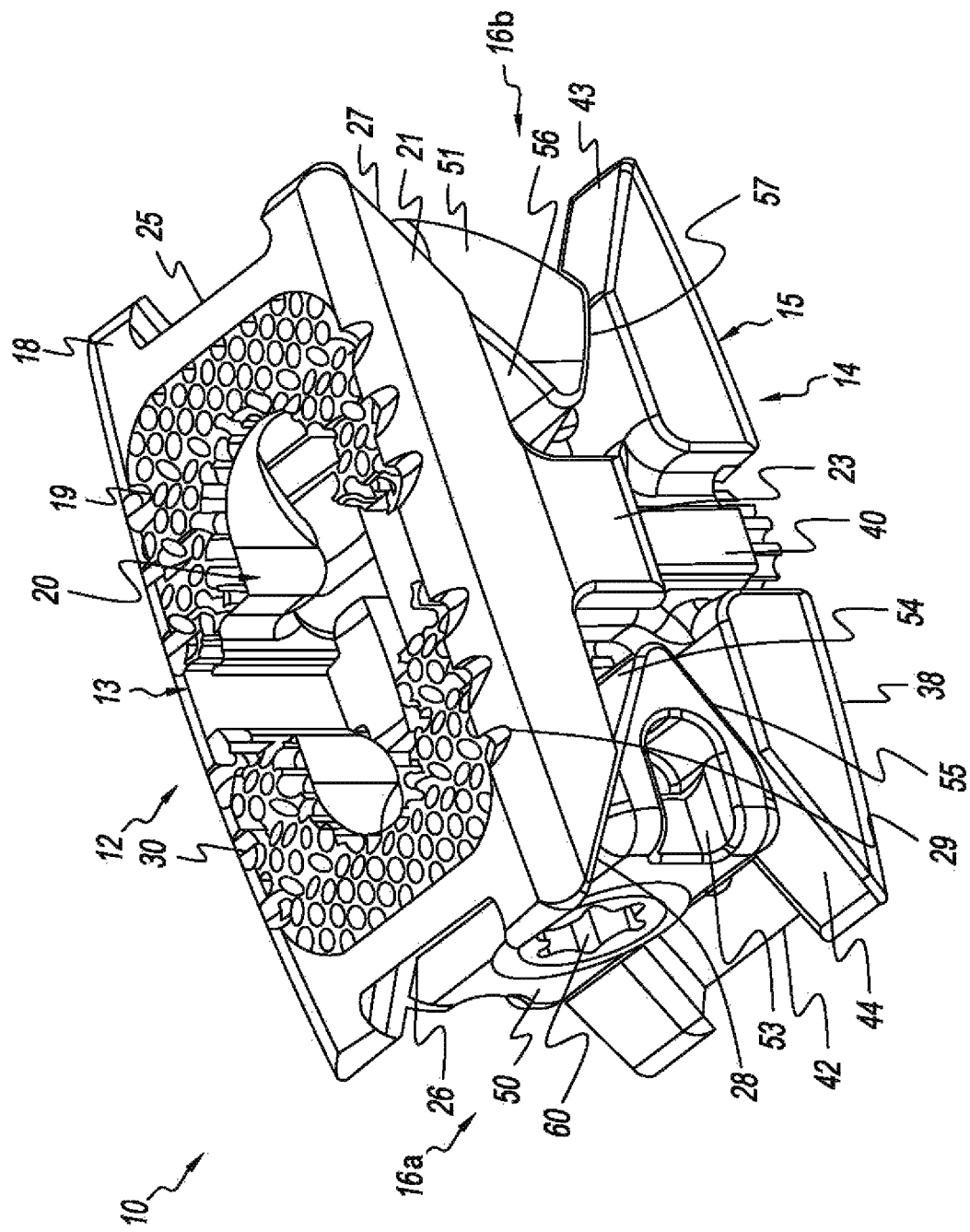
FIG. 2 is another isometric view of the intervertebral spine implant of FIG. 1, upside down and reversed relative to FIG. 1.
Figure 3:
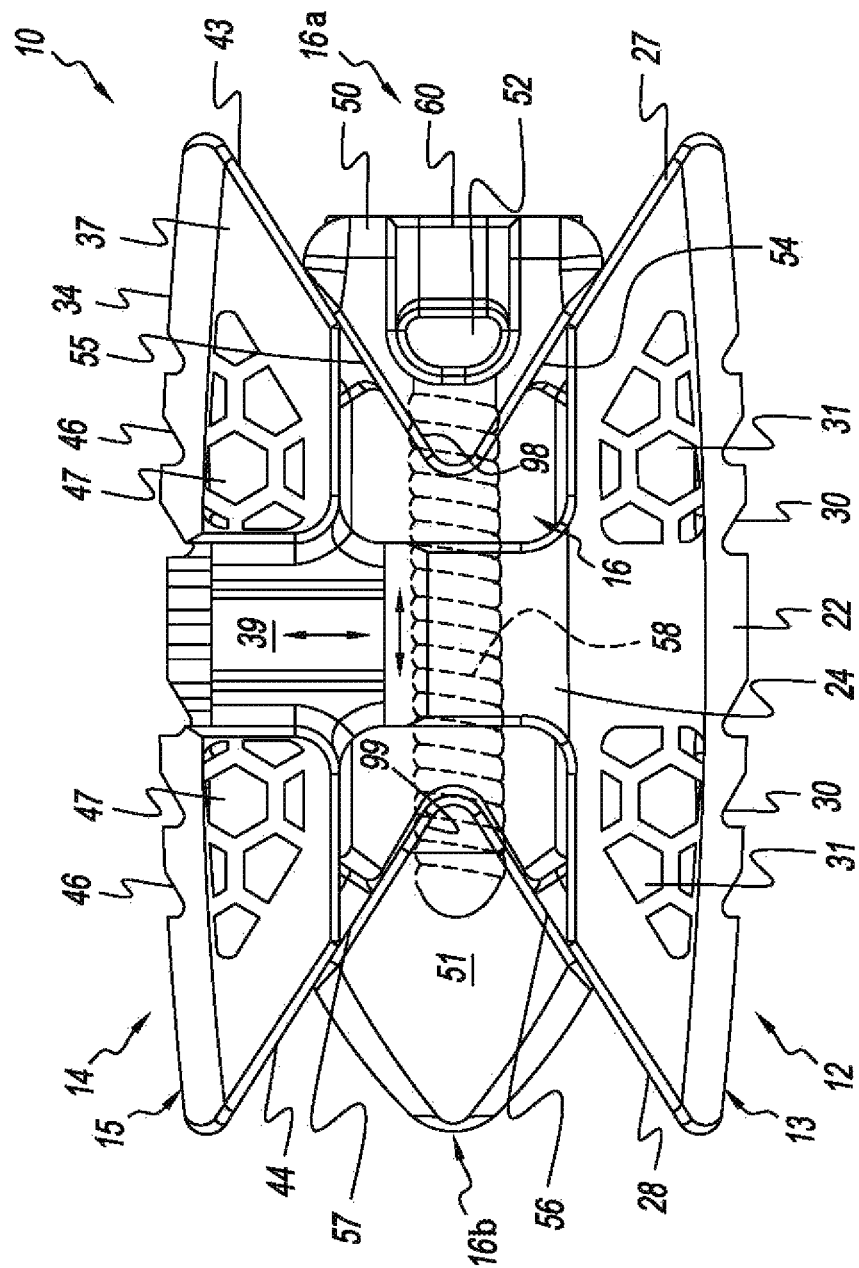
FIG. 3 is a side view of the intervertebral spine implant of FIG. 1.

FIGS. 1-3 depict one form of a height adjustable intervertebral (interbody) spine implant (intervertebral spine implant) 10 fashioned in accordance with the present principles. The intervertebral spine implant 10 is characterized by a first component 12, a second component 14, and height adjustment means, adjustor, adjustment mechanism, controllable drive, control drive, drive mechanism, screw drive, or the like (height adjustment mechanism) 16 all made from one or more bio-compatible materials. The first and second components 12, 14 are movable with respect to one another through manipulation of the height adjustment mechanism 16. The first component 12, the second component 14, and/or the height adjustment mechanism 16 may be 3-D printed, machined, or otherwise manufactured, as well as conventionally.

The first component 12 may be either the lower, inferior, or caudal component configured to abut a lower, inferior, or caudal vertebra or vertebral surface (not shown), or the upper, superior, or cephalad component configured to abut an upper, superior, or cephalad vertebra or vertebral surface (not shown), while accordingly, the second component 14 may be either the upper, superior, or cephalad component configured to abut an upper, superior, or cephalad vertebra or vertebral surface (not shown), or the lower, inferior, or caudal component configured to abut a lower, inferior, or caudal vertebra or vertebral surface (not shown). In both cases, the height adjustment mechanism 16 is user-operable to effect movement of the first and second components 12, 14 relative to one another via first and second opposing wedges 50, 51 so as to effect height adjustment (taller or shorter) of the intervertebral spine implant 10. Without limitation, the first component 12 will hereinafter be discussed as being the lower component, while the second component 14 will be discussed as being the upper component, it being understood that the first component can be the upper component and the second component can be the lower component.

The first component 12 is characterized by a base, platform, body or the like 13 fashioned generally as a trapezoid having one side of parallel sides of a generally planar contact surface 18 that is configured to abut/contact a bone, boney surface, vertebral surface, vertebra, or the like (not shown) the other side of the parallel sides not discerned but opposite the side 18. The contact surface 18 includes an area 19 of a matrix, mesh, perforations, holes, openings, pores, or the like (collectively, matrix) that aid in fusion. The matrix 19 surrounds a bore 20 that extends through the body 13. The matrix area 19 may be modified in pattern, placement and/or structure as desired or needed. The body 13 is further characterized by a first lateral or side rail 21 and a second lateral or side rail 22, the nomenclature first and second being arbitrary. A boss 23 extends from a middle portion of the first lateral side rail 21, the boss 23 configured to receive a flange 40 of a first lateral side rail 38 of the second component 14, while a boss 24 extends from a middle portion of the second lateral side rail 22, the boss 24 configured to receive a flange 39 of a first lateral side rail 37 of the second component 14. Notches 29 are formed on the top of the first lateral side rail 21 to, at least, aid in retention and/or insertion of the body 13, while notches 30 are formed on the top of the second lateral side rail 22 to, at least, aid in retention and/or insertion of the body 13. A cutout 25 is formed on one or first end 70 of the body 13 at the contact surface 18, while a cutout 26 is formed on the other or second end 71 of the body 13 at the contact surface 18. In the form shown, the first lateral side rail 21 is shown without a matrix (as defined above) while the lateral side rail 22 is shown with a matrix 31 (as defined above). It should be appreciated that both side rails 21, 22 may or may not have a matrix, thereby creating more forms of the invention. The contact surface 18 is the long side and the surface 62 is the short side of the parallel sides.

In accordance with an aspect of the invention, a surface 27 is defined as one of the skew sides of the trapezoid body 13 that is adjacenet the cutout 25 and below the contact surface 18 while a surface 28 is defined as another one of the skew sides of the trapezoid body 13 that is adjacent the cutout 26 and below the contact surface 18. The surface 27 slopes or angles inwardly. The surface 28 slopes or angles inwardly. These surfaces 27, 28 are contact surfaces for the wedges 50, 51.

The second component 14 is characterized by a base, platform, body or the like 15 fashioned generally as a trapezoid having one side of parallel sides of a generally planar contact surface 34 that is configured to abut/contact a bone, boney surface, vertebral surface, vertebra, or the like (not shown) the other side of the parallel side 61 opposite the side 34. The contact surface 34 includes an area 35 of a matrix, mesh, perforations, holes, openings, pores, or the like (collectively, matrix) that aid in fusion. The matrix 35 surrounds a bore 36 that extends through the body 15. The matrix area 35 may be modified in pattern, placement and/or structure as desired or needed. The body 15 is further characterized by a third lateral or side rail 37 and a fourth lateral or side rail 38. A flange 39 extends from a middle portion of the third lateral side rail 37, the flange 39 configured to be received in the boss 24 of the lateral side rail 22 of the first component 12, while a flange 40 extends from a middle portion of the fourth lateral side rail 38, the flange 40 configured to be received in the boss 23 of the lateral side rail 21 of the first component 14. Notches 45 are formed on the top of the side rail 37 to, at least, aid in retention and/or insertion of the body 15, while notches 46 are formed on the top of the side rail 38 to, at least, aid in retention and/or insertion of the body 15. A cutout 41 is formed on one or first end 72 of the body 15 at the contact surface 34, while a cutout 42 is formed on the other or second end 73 of the body 15 at the contact surface 34. In the form shown, the lateral side rail 38 is shown without a matrix (as defined above) while the lateral side rail 37 is shown with a matrix 47 (as defined above). It should be appreciated that both side rails 37, 38 may or may not have a matrix, thereby creating more forms of the invention. The contact surface 34 is the long side and the surface 61 is the short side of the parallel sides.

In one form, the height adjustment means 16 may be characterized by a first wedge 50 situated between the surface 27 of the skew side of the first component 12 and the surface 43 of the skew side of the second component 14 thereby forming a first pocket 16a, a second wedge 51 situated between the skew surface 28 of the first component 12 and the skew surface 44 of the second component 14 thereby forming a second pocket 16b, the nomenclature first and second being arbitrary, and a drive screw or the like 58 connected between the first and second wedges 50, 51 and, in particular, is connected to threaded bores/openings 98, 99 in the first and second wedges 50, 51, the threaded openings being reverse threaded relative to one another in order for the drive screw 58 to concertedly move the first and second wedges 50, 51 either towards or away from each other depending on the rotational direction of the drive screw 58. In another form, the drive screw may constitute the height adjustment mechanism for the first and second wedges 50, 51. The first wedge 50 includes a first lateral opening 50 and a second lateral opening 51 opposite the first lateral opening 50, the nomenclature first and second being arbitrary. The second wedge 51 does not have lateral openings but can if desired. A socket 60 is situated at an end of the drive screw 58 that is configured to receive a drive tool (not shown) for rotating the drive screw 58 to adjust implant height. Rotation of the drive screw 58 in one direction increases implant height by bringing the first and second wedges 50, 51 toward each other (contraction), while rotation of the drive screw 58 in the opposite direction decreases implant height by spreading the first and second wedges 50, 51 away from each other (expansion).

The first wedge 50 has a first sloped or angled surface 54 and a second sloped or angled surface 55 opposite the first sloped surface 54, the nomenclature first and second being arbitrary. The first sloped surface 54 abuts the angled surface (skew side) 27 of the first component 12, while the second sloped surface 55 abuts the angled surface (skew side) 43 of the second component 14. The second wedge 51 has a third sloped or angled surface 56 and a fourth sloped or angled surface 57 opposite the third sloped surface 56, the nomenclature third and fourth being arbitrary. The third sloped surface 56 abuts the angled surface (skew side) 27 of the first component 12, while the fourth sloped surface 57 abuts the angled surface (skew side) 43 of the second component 14.

As the first and second wedges 50, 51 are pulled together by rotation of the drive screw 58 via a drive tool (not shown) in the socket 60 in one direction, the wedges 50, 51 move within the respective first and second pockets to push against the first and second components 12, 14 to expand them relative to one another in order to increase implant height. As the first and second wedges 50, 51 are pushed away by rotation of the drive screw 58 via the drive tool in the socket 60 in the opposite direction, the wedges 50, 51 move within the respective first and second pockets to relieve pressure against the first and second components 12, 14 to allow them to contract relative to one another in order to decrease implant height.

Figure 4:
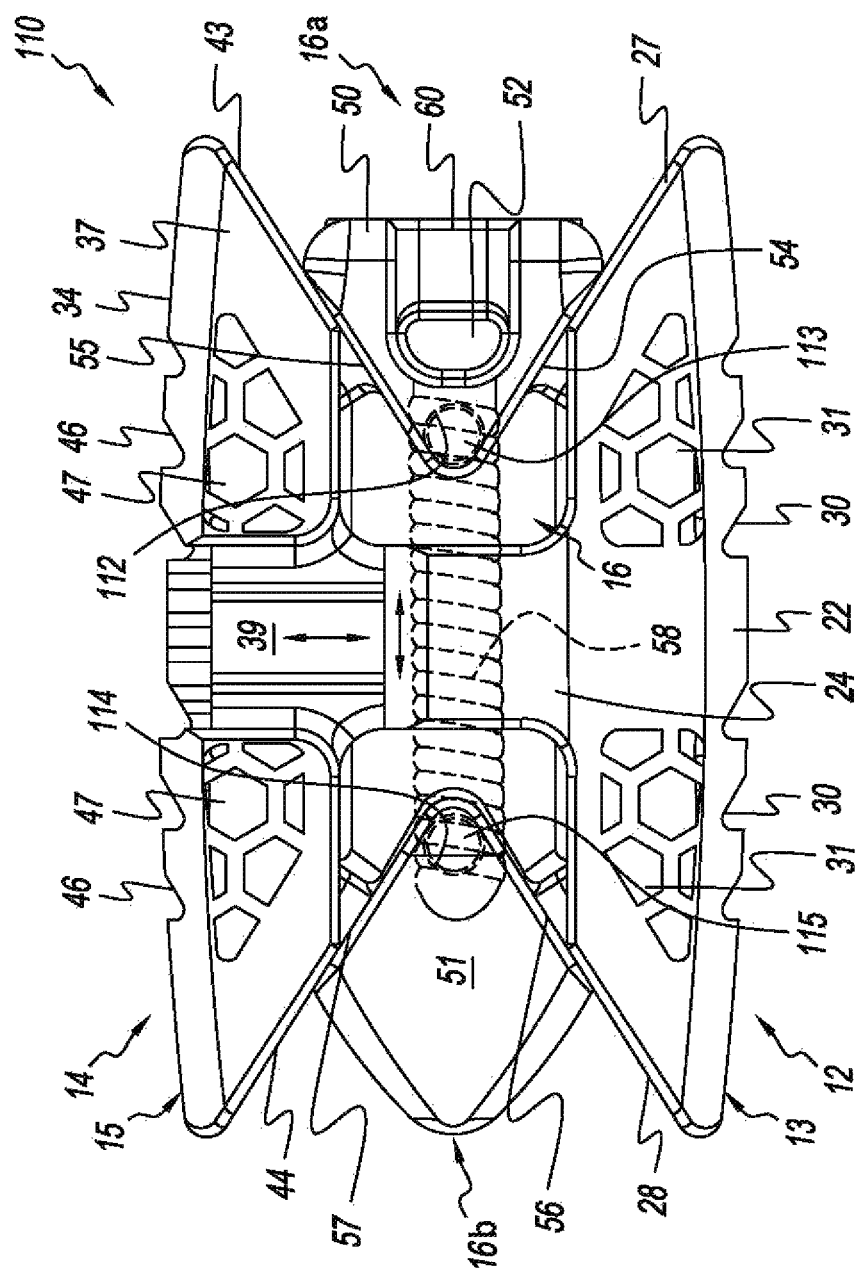
FIG. 4 is an isometric view of another form of an intervertebral spine implant fashioned in accordance with the present principles.

FIG. 4 depicts another form of an intervertebral spine implant 110 fashioned in accordance with the present principles that has the exact same components as the intervertebral spine implant 10, and thus has the same numbering and therefore function, configuration and description as the intervertebral spine implant 10 with the exception of the following additional components. The first wedge 50 has a spherical pocket 112 disposed at its apex with a ball 113 disposed therein. The second wedge 51 has a spherical pocket 114 disposed at its apex with a ball 115 disposed therein. The ball 113 has a threaded bore therein. The ball 115 also has a threaded bore therein that is opposite in threading to the threading of the threaded bore of the ball 113. The drive screw 58 extends through the threaded bore of the ball 113 and the threaded bore of the threaded bore of the ball 115. Rotation of the drive screw 58 in one direction pulls the first and second wedges 50, 51 together to effect an increase in height of the intervertebral spine implant 110, while rotation of the drive screw 58 in the opposite direction pushes the first and second wedges 50, 51 away to effect a decrease in height of the intervertebral spine implant 110.

It should furthermore be appreciated that dimensions of the components, structures, and/or features of the present static fixation strut may be altered as desired within the scope of the present disclosure.

What is claimed is:

1. A height adjustable intervertebral spine implant, comprising:

a first trapezoidal component defining a first surface of a first length with a first lateral side and a second lateral side opposite the first lateral side, a second surface opposite and parallel to the first surface having a second length that is less than the first length of the first surface with a third lateral side and a fourth lateral side opposite the third lateral side, a first inwardly sloping surface at a first end of and between the first surface and the second surface, and a second inwardly sloping surface at a second end of and between the first surface and the second surface opposite the first end, the first and second inwardly sloping surfaces skew to each other;

a first boss extending from the first lateral side of the first surface of the first trapezoidal component;

a second boss extending from the second lateral side of the first surface of the first trapezoidal component;

a second trapezoidal component defining a third surface of a third length with a third lateral side and a fourth lateral side opposite the third lateral side, a fourth surface opposite and parallel to the third surface having a fourth length that is less than the third length of the third surface with a fifth lateral side and a sixth lateral side opposite the fifth lateral side, a third inwardly sloping surface at a third end of and between the third surface and the fourth surface, and a fourth inwardly sloping surface at a fourth end of and between the third surface and the fourth surface opposite the third end, the third and fourth surfaces skew to each other;

a first flange extending from the third lateral side of the third surface of the second trapezoidal component and configured for movable reception in the first boss of the first trapezoidal component;

a second flange extending from the fourth lateral side of the fourth surface of the second trapezoidal component and configured for movable reception in the second boss of the first trapezoidal component;

the first and second trapezoidal components oriented such that the fourth surface of the second trapezoidal component is adjacent the second surface of the first trapezoidal component, the first flange of the second trapezoidal component is movably received in the first boss of the first trapezoidal component and the second flange of the second trapezoidal component is movably received in the second boss of the first trapezoidal component, whereby the first and second trapezoidal components are translatable relative to each other;

a first wedge disposed between the first inwardly sloping surface at the first end of and between the first surface and the second surface of the first trapezoidal component and the third inwardly sloping surface at the third end of and between the third surface and the fourth surface of the second trapezoidal component;

a second wedge disposed between the second inwardly sloping surface at the second end of and between the first surface and the second surface of the first trapezoidal component and the fourth inwardly sloping surface of the fourth end of and between the third surface and the fourth surface of the second trapezoidal component;
a drive mechanism coupled to the first wedge and to the second wedge and operative to concertedly pull the first and second wedges together to effect expansion of the first and second trapezoidal components relative to each other to increase height of the intervertebral spine implant, and to concertedly spread the first and second wedges apart to effect contraction of the of the first and second trapezoidal components relative to each other to decrease height of the intervertebral spine implant;
a first spherical pocket disposed in the first wedge;
a second spherical pocket disposed in the second wedge;
a first ball having a first threaded bore and situated in the first spherical pocket;
a second ball having a second threaded bore and situated in the second spherical pocket; and
the drive mechanism having a threaded screw received in the first threaded bore of the first ball of the first wedge and in the second threaded bore of the second ball of the second wedge and operative through rotation in one direction to effect expansion of the first and second trapezoidal components relative to one another and in another direction to effect contraction of the first and second trapezoidal components.

2. The height adjustable intervertebral spine implant of claim 1, wherein:
the first threaded bore of the first ball is threaded with a threading of a first rotational direction; and
the second threaded bore of the second ball is threaded with a threading of a second rotation direction that is opposite the first rotational direction.

3. An intervertebral spine implant comprising:
a first trapezoidal component defining a first surface of a first length with a first lateral side and a second lateral side opposite the first lateral side and adapted to abut a first vertebral surface, a second surface opposite and parallel to the first surface having a second length that is less than the first length of the first surface with a third lateral side and a fourth lateral side opposite the third lateral side, a first inwardly sloping surface at a first end of and between the first surface and the second surface, and a second inwardly sloping surface at a second end of and between the first surface and the second surface opposite the first end, the first and second inwardly sloping surfaces skew to each other;
a first boss extending from the first lateral side of the first surface of the first trapezoidal component;
a second boss extending from the second lateral side of the first surface of the first trapezoidal component;
a second trapezoidal component defining a third surface of a third length with a third lateral side and a fourth lateral side opposite the third lateral side and adapted to abut a second vertebral surface, a fourth surface opposite and parallel to the third surface having a fourth length that is less than the third length of the third surface with a fifth lateral side and a sixth lateral side opposite the fifth lateral side, a third inwardly sloping surface at a third end of and between the third surface and the fourth surface, and a fourth inwardly sloping surface at a fourth end of and between the third surface and the fourth surface opposite the third end, the third and fourth surfaces skew to each other;
a first flange extending from the third lateral side of the third surface of the second trapezoidal component and configured for movable reception in the first boss of the first trapezoidal component;
a second flange extending from the fourth lateral side of the fourth surface of the second trapezoidal component and configured for movable reception in the second boss of the first trapezoidal component;
the first and second trapezoidal components oriented such that the fourth surface of the second trapezoidal component is adjacent the second surface of the first trapezoidal component, the first flange of the second trapezoidal component is movably received in the first boss of the first trapezoidal component and the second flange of the second trapezoidal component is movably received in the second boss of the first trapezoidal component, whereby the first and second trapezoidal components are translatable relative to each other;
a first wedge-shaped pocket defined between the first inwardly sloping surface at a first end of and between the first surface and the second surface of the first trapezoidal component and the third inwardly sloping surface at a third end of and between the third surface and the fourth surface of the second trapezoidal component
a first wedge disposed in the first wedge-shaped pocket;
a second wedge-shaped pocket defined between the second inwardly sloping surface at a second end of and between the first surface and the second surface of the first trapezoidal component and the fourth inwardly sloping surface of a fourth end of and between the third surface and the fourth surface of the second trapezoidal component;
a second wedge disposed in the second wedge-shaped pocket;
a threaded screw coupled to the first wedge and to the second wedge and operative to concertedly pull the first and second wedges together to effect expansion of the first and second trapezoidal components relative to each other to increase height of the intervertebral spine implant, and to concertedly spread the first and second wedges apart to effect contraction of the of the first and second trapezoidal components relative to each other to decrease height of the intervertebral spine implant;
a first spherical pocket disposed in the first wedge;
a second spherical pocket disposed in the second wedge;
a first ball having a first threaded bore and situated in the first spherical pocket;
a second ball having a second threaded bore and situated in the second spherical pocket; and
the threaded screw received in the first threaded bore of the first ball of the first wedge and in the second threaded bore of the second ball of the second wedge and operative through rotation in one direction to effect expansion of the first and second trapezoidal components relative to one another and in another direction to effect contraction of the first and second trapezoidal components.

4. The intervertebral spine implant of claim 3, wherein:
the first threaded bore of the first ball is threaded with a threading of a first rotational direction; and
the second threaded bore of the second ball is threaded with a threading of a second rotation direction that is opposite the first rotational direction.

* * * * *